US012624272B2

(12) United States Patent
Darugar et al.

(10) Patent No.: US 12,624,272 B2
(45) Date of Patent: May 12, 2026

(54) POURABLE WETTING AGENTS AND METHODS ASSOCIATED THEREWITH

(71) Applicant: SAUDI ARABIAN OIL COMPANY, Dhahran (SA)

(72) Inventors: Qusai A. Darugar, Cypress, TX (US); Ashok Santra, The Woodlands, TX (US); Nicolas Osorio, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 18/679,317

(22) Filed: May 30, 2024

(65) Prior Publication Data

US 2025/0368881 A1 Dec. 4, 2025

(51) Int. Cl.

*C09K 8/36* (2006.01)
*C07D 233/24* (2006.01)
*E21B 21/00* (2006.01)

(52) U.S. Cl.

CPC .............. *C09K 8/36* (2013.01); *C07D 233/24* (2013.01); *E21B 21/003* (2013.01)

(58) Field of Classification Search

CPC ...... C09K 8/035; C09K 8/03; C09K 2208/34; C09K 8/24; C09K 8/36; C09K 8/04; C09K 8/32; C09K 23/16; C09K 8/467; C09K 8/506; C09K 8/28; C09K 8/74; E21B 21/00; E21B 21/003

See application file for complete search history.

(56) References Cited

U.S. PATENT DOCUMENTS

| | | | | |
|---|---|---|---|---|
| 4,508,628 | A | 4/1985 | Walker et al. | |
| 6,006,831 | A | 12/1999 | Schlemmer et al. | |
| 8,163,675 | B2 | 4/2012 | Navarrete et al. | |
| 10,597,570 | B2 | 3/2020 | Hurd et al. | |
| 2017/0002252 | A1* | 1/2017 | Ng | C09K 8/32 |
| 2018/0194988 | A1 | 7/2018 | Hilfiger et al. | |
| 2020/0291286 | A1 | 9/2020 | Hilfiger et al. | |
| 2023/0374365 | A1* | 11/2023 | Khramov | C09K 8/36 |

FOREIGN PATENT DOCUMENTS

| | | | | |
|---|---|---|---|---|
| CN | 105593341 | B | 8/2018 | |
| EP | 3036311 | B1 | 9/2018 | |
| WO | WO-9634069 | A1 * | 10/1996 | C10M 135/54 |

OTHER PUBLICATIONS

Khramov et al., "Designing Advanced Emulsifiers for High-Performance Synthetic Fluids: From Drawing Board to the Challenging Wells," AADE-20-FTCE-085, 8 pages.

Khaklari et al., "A Review of Various Pour Point Depressants Used for Flow Assurance in Oil Industries," International Journal of Engineering Applied Sciences and Technology, 2021, vol. 6 Issue 1, pp. 335-352.

Al-Yami et al., "Emulsifiers Used in Designing Emulsion Based Drilling Fluids," Research & Reviews: Journal of Chemistry, e-ISSN:2319-9849, Published Nov. 11, 2018, 12 pages.

* cited by examiner

*Primary Examiner* — Zakiya W Bates

(74) *Attorney, Agent, or Firm* — Vorys, Sater, Seymour and Pease, LLP

(57) ABSTRACT

Pourable wetting agent compositions include a first condensation reaction product having a structure represented by the formula $R''—NH—CH_2—(CH_2NR''CH_2)_a—CH_2—C_3H_4N_2—R'$;

wherein a is 0 or a positive integer; R' is a $C_6$-$C_{30}$ hydrocarbyl group; and R'' is-CO—R' or —CO-A-COOH, provided that at least one occurrence of R'' is-CO-A-COOH; wherein A is a divalent hydrocarbyl group.

8 Claims, 2 Drawing Sheets

POURABLE WETTING AGENTS AND METHODS ASSOCIATED THEREWITH

FIELD OF THE DISCLOSURE

The present disclosure relates generally to oil-based drilling fluids and, more particularly, to oil-based drilling fluids containing wetting agents.

BACKGROUND OF THE DISCLOSURE

Drilling fluids, also referred to as drilling muds, are integral to the success of drilling programs, fulfilling several crucial functions. Drilling fluids are designed to maintain optimal wellbore pressure, provide cooling and lubrication to the drill bit, and facilitate the removal of solids and drill cuttings from the wellbore. Initial mud systems, comprising water and clay, remain in use today. However, these fluids are characterized by a reduced penetration rate and have the potential to interact adversely with clay and shale sections of subterranean formations, leading to complications such as wellbore collapse and stuck pipe, for example. To counteract these issues, drilling fluids based on non-aqueous or oil-based formulations have been developed.

Early oil-based drilling fluids were deployed for reactive formations and to enhance drilling performance; however, these drilling fluids fell short in terms of possessing fluid properties suitable for operations under higher temperatures and pressures and lacked an effective supporting fluid structure to promote removal of drill cuttings from the borehole. To rectify the foregoing challenges, invert emulsion drilling fluids containing chemical additives (e.g., emulsifiers/emulsifying agents) to facilitate mixing of otherwise immiscible components (e.g., oil and water) have been developed.

Oil-based drilling fluids have recently enjoyed significant improvements through the incorporation of additional chemical additives to enhance the fluids' performance in extreme conditions, including elevated temperatures and pressures. Despite these advancements, the emulsifying agents used have seen minimal change. Traditionally, drilling fluids have incorporated a combination of a primary emulsifier and a secondary emulsifier (e.g., a wetting agent).

Primary emulsifiers commonly comprise complex mixtures derived from animal fats or oleaginous byproducts, such as tall oil from the pulp industry, for example. These low-cost commodity chemicals are typically used as-procured, without further chemical modification.

Wetting agents play a critical role in the formulation of modern drilling fluids, especially in oil-based drilling fluid systems comprising an oil-based emulsion. Unfortunately, some wetting agents are notoriously viscous and are often not pourable from a storage container at ambient temperatures, thereby complicating the preparation of oil-based drilling fluids. Therefore, there exists a need for less viscous wetting agents that are still capable of maintaining the enhanced performance of modern oil-based drilling fluids.

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

According to an embodiment consistent with the present disclosure, pourable wetting agent compositions include a first condensation reaction product having a structure represented by

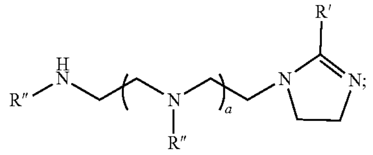

wherein: a is 0 or a positive integer; R' is a $C_6$-$C_{30}$ hydrocarbyl group; and R" is —CO—R' or —CO-A-COOH, provided that at least one occurrence of R" is —CO-A-COOH; wherein A is a divalent hydrocarbyl group.

In another embodiment, methods associated with pourable wetting agents include providing a composition comprising a first amidated imidazoline having a structure represented by

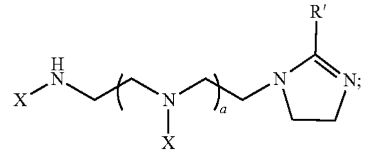

wherein a is 0 or a positive integer; R' is a $C_6$-$C_{30}$ hydrocarbyl group; and X is H or —CO—R', provided that at least one occurrence of X is H; combining the composition with a dicarboxylic acid having a formula of HOOC-A-COOH to form a reaction mixture; wherein A is a divalent hydrocarbyl group; and heating the reaction mixture at a first reaction temperature for a first time period to form a second amidated imidazoline having a structure represented by

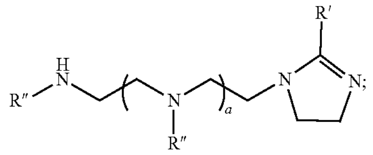

wherein: a is 0 or a positive integer; R' is a $C_6$-$C_{30}$ hydrocarbyl group; and R" is —CO—R' or —CO-A-COOH, provided that at least one occurrence of R" is —CO-A-COOH.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Figure 1A:
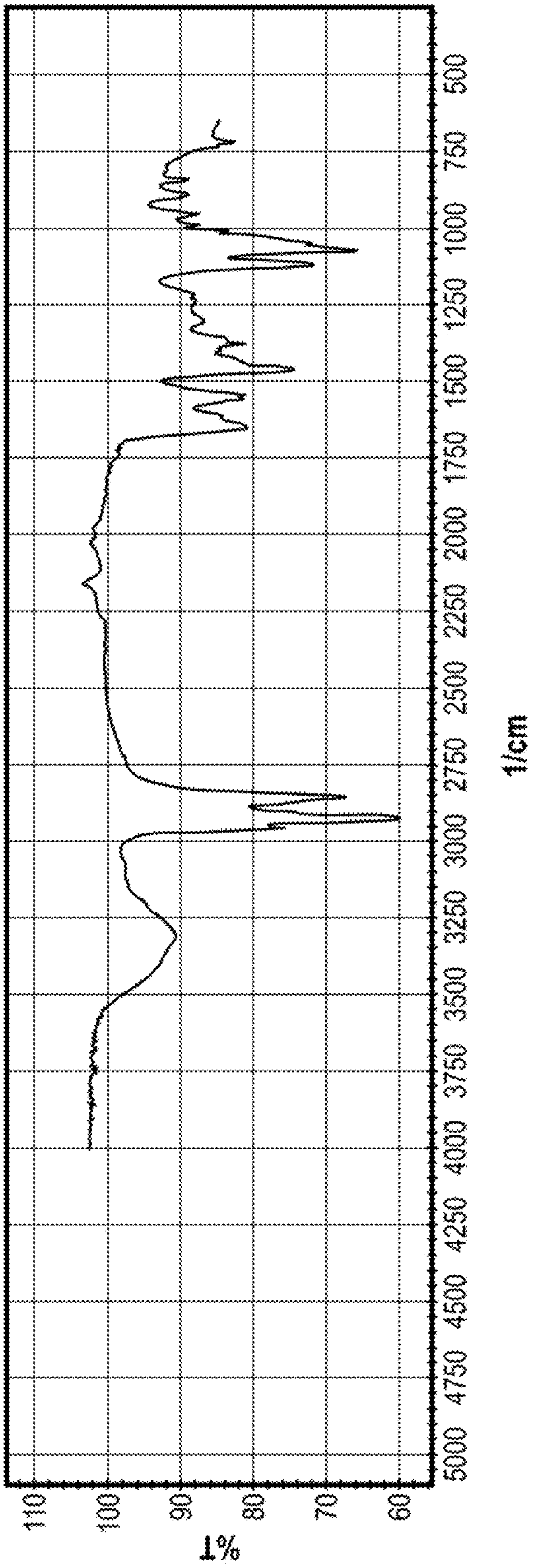
FIG. 1A is an illustrative FTIR spectrum of an amidated imidazoline.

Embodiments in accordance with the present disclosure generally relate to oil-based drilling fluids and, more particularly, to oil-based drilling fluids containing wetting agents.

As discussed above, conventional wetting agents often present significant handling challenges due to their high viscosity values at ambient temperature. The present disclosure addresses the foregoing challenge by providing wetting agent compositions that are pourable at ambient temperatures, while still maintaining other desirable performance features of the wetting agents. The wetting agents described herein may be used as components of oil-based drilling fluids. Such drilling fluids may exhibit similar or even improved performance compared to drilling fluids comprising conventional wetting agents.

Wetting agents of the present disclosure are compositions formed from an amidated imidazoline and/or an amidated polyamine through a condensation reaction with a dicarboxylic acid.

Compositions of the present disclosure may comprise a first condensation reaction product having a structure represented by Formula 1.

Formula 1

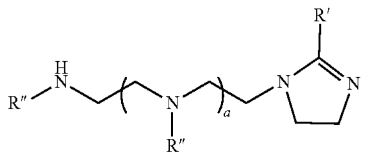

In Formula 1, a is 0 or a positive integer, R' is a $C_6$-$C_{30}$ hydrocarbyl group, and R" is —CO—R' or —CO-A-COOH, with the provision that at least one occurrence of R" is —CO-A-COOH. Variable A is a divalent hydrocarbyl group and is derived from a dicarboxylic acid, in which the two carboxylic acid groups are linked by the divalent hydrocarbyl group.

The compositions may further comprise a second condensation reaction product having a structure represented by Formula 2.

Formula 2

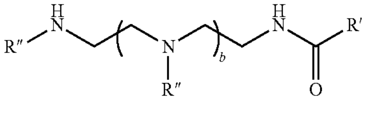

In Formula 2, b is a positive integer, and R', R", and A are defined as in Formula 1 (i.e., R' is a $C_6$-$C_{30}$ hydrocarbyl group, and R" is —CO—R' or —CO-A-COOH, with the provision that at least one occurrence of R" is —CO-A-COOH, and A is a divalent hydrocarbyl group).

In the first and second condensation reaction products, R', R", and A may be the same or different. Preferably, R', R", and A are the same, if both the first condensation reaction product and the second condensation reaction product are present.

In the first condensation reaction product, a is preferably 0, 1, or 2. More preferably, a is 1 or 2.

If the second condensation reaction product is present, b is preferably 1, 2, or 3. More preferably, b is 2 or 3. In various examples, b=a+1.

If both the first and second condensation reaction products are present, a and b may be selected such that the first and second condensation reaction products have the same or different numbers of nitrogen atoms. Preferably, a and b are selected such that the first and second condensation reaction products have the same number of nitrogen atoms, if both the first condensation reaction product and the second condensation reaction product are present in the composition.

The first condensation reaction product may be present alone or in combination with the second condensation reaction product. The second condensation reaction product may be present alone or in combination with the first condensation reaction product. A ratio of the first condensation reaction product to the second condensation reaction product may therefore range from 0:100 to 100:0, including any sub-range in between these values. When both the first condensation reaction product and the second condensation reaction product are present, either the first condensation reaction product or the second condensation reaction product may be present as a majority component.

The divalent hydrocarbyl group defining A may be optionally branched and/or optionally unsaturated. In more specific examples, the hydrocarbyl group may be a $C_1$-$C_3$ alkyl group, a $C_2$-$C_3$ alkenyl group, or a $C_2$-$C_3$ alkynyl group. In more specific examples, the hydrocarbyl group defining A may be a $C_2$-$C_3$ cis-alkenyl group.

The $C_6$-$C_{30}$ hydrocarbyl group defining R' may be optionally branched and/or optionally unsaturated. In some examples, R' may be a $C_6$-$C_{30}$ alkyl group. In more specific examples, R' may be a $C_6$-$C_{10}$ alkyl group, or a $C_{10}$-$C_{18}$ alkyl group, or a $C_{18}$-$C_{30}$ alkyl group. In still more specific examples, R' may be a $C_{10}$-$C_{14}$ alkyl group, or a $C_{12}$-$C_{14}$ alkyl group. Corresponding alkenyl and/or alkynyl groups having the same number of carbon atoms may be present as R'.

Compositions of the present disclosure may be prepared from amidated imidazolines prepared from a polyamine and/or amidated polyamines by performing a condensation reaction with a dicarboxylic acid. More specifically, such methods may comprise:

providing a composition comprising a first amidated imidazoline having a structure represented by Formula 3

Formula 3

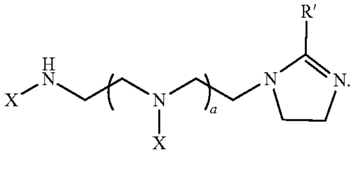

In Formula 3, X is H or —CO—R', with the provision that at least one occurrence of X is H, and the other variables are defined as above for Formula 1 (i.e., a is 0 or a positive integer, and R' is a $C_6$-$C_{30}$ hydrocarbyl group). The composition is contacted with a dicarboxylic acid having a formula of HOOC-A-COOH (A is a divalent hydrocarbyl group as defined above for Formula 1) to form a reaction mixture. The reaction mixture is then heated at the first reaction temperature for a first time period to form a second amidated imidazoline having a structure represented by Formula 1.

Examples of suitable dicarboxylic acids may include, but are not limited to, maleic acid, fumaric acid, succinic acid, malonic acid, glutaric acid, glutaconic acid, 1,4-butynedicarboxylic acid, the like, and any combination thereof. More preferably, the dicarboxylic acid is unsaturated. Preferably, unsaturated dicarboxylic acids have a cis-configuration about their olefinic double bond. Unsaturated dicarboxylic acids having a cis-configuration may form a 7-membered internal hydrogen bond.

The compositions formed in the condensation reaction may further comprise a first amidated polyamine having a structure represented by Formula 4

Formula 4

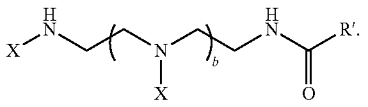

In Formula 4, X is H or —CO—R', provided that at least one occurrence of X is H, and the other variables are defined as above for Formula 2 (i.e., b is a positive integer, and R' is a $C_6$-$C_{30}$ hydrocarbyl group). When contacted with a dicarboxylic acid at the first reaction temperature for the first time period, a second amidated polyamine having a structure represented by Formula 2 may be formed.

Without being bound by theory or mechanism, the first reaction temperature may be sufficient to promote a condensation reaction between the first amidated imidazoline and the dicarboxylic acid to form the second amidated imidazoline, and between the first amidated polyaminc (if present) and the dicarboxylic acid to form the second amidated polyaminc. In some examples, the first reaction temperature may be at least about 180° C. and the first time period may be at least about 5 hours. Preferably, the first reaction temperature and the first time period may be sufficient to convert substantially all free amines of the first amidated imidazoline and the first amidated polyamine (if present) into an amidated form.

The first amidated imidazoline and the first amidated polyamine (if present) may be formed via a condensation reaction of a polyamine and a fatty acid having a formula of R'—COOH, wherein R' is defined as above. In non-limiting examples, polyamines such as diethylenetriamine, triethylenetetramine, tetracthylenepentamine, or any combination thereof may be used to form the first amidated imidazoline and/or the first amidated polyaminc.

Accordingly, in some examples, methods of the present disclosure may comprise: contacting a fatty acid having a formula of R'—COOH with a polyamine in the presence of an acid catalyst (e.g., an organic acid such as p-toluenesulfonic acid), forming a first amidated polyamine under a first set of conditions, and converting at least a portion of the first amidated polyamine to a first amidated imidazoline under a second set of conditions. The first amidated polyamine may have a structure represented by Formula 4 above, and the first amidated imidazoline may have a structure represented by Formula 3 above.

Without being bound by theory or mechanism, the first set of conditions may be sufficient to promote a condensation reaction between the polyamine and the fatty acid, thereby forming the first amidated polyamine. The first set of conditions may comprise a second reaction temperature of at least about 160° C. and a second time period of at least about 4 hours.

In some or other examples, the first set of conditions may comprise a second temperature of at least about 160° C., or at least about 170° C., or at least about 180° C., and/or a second time period of least about 4 hours, or at least about 5 hours, or at least about 6 hours.

Continuing to be unbound by theory or mechanism, the second set of conditions may convert the first amidated polyamine or a portion thereof to the first amidated imidazoline, which may then undergo conversion to the second imidazoline, as discussed in more detail above. The second set of conditions may comprise a third reaction temperature of at least about 180° C. and a third time period of about 2 hours to about 3 hours. It is to be appreciated that higher or lower reaction temperatures may be used and/or shorter or longer time periods may be used, and such variables may be manipulated to determine the extent to which the first amidated polyamine is converted into the first amidated imidazoline. That is, the second set of conditions may promote formation of the first amidated imidazoline alone, or a mixture of the first amidated imidazoline and residual first amidated polyamine. When the mixture is produced under the second set of conditions, the mixture may be converted into a composition comprising both the second amidated imidazoline having Formula 3 and the second amidated polyamine having Formula 4.

In some or other examples, the second set of conditions may comprise a third temperature that is higher than the second temperature and a third time period that may be shorter or longer than the second time period. For example, the third temperature may be at least about 180° C., or at least about 190° C., or at least about 200° C., and/or the third time period may be about 2 hours to about 3 hours, or about 2 hours to about 2.5 hours, or about 2.5 hours to about 3 hours.

Accordingly, second amidated imidazolines that may be formed in the present disclosure may include, but are not limited to:

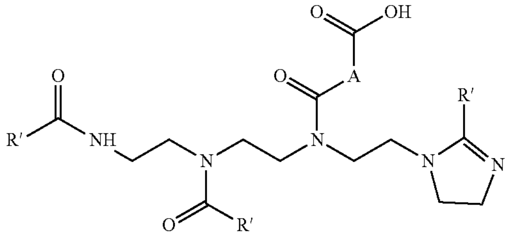

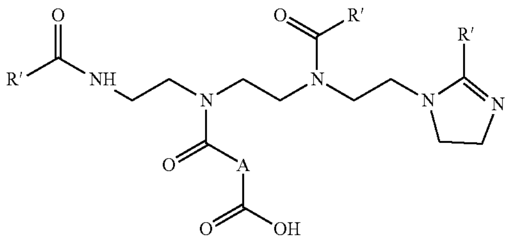

-continued

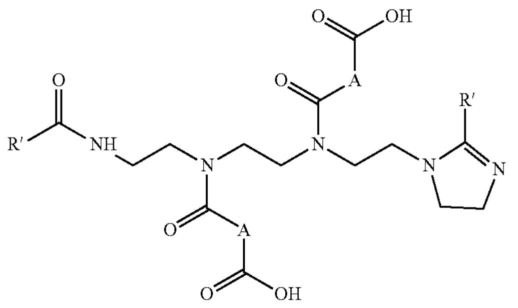

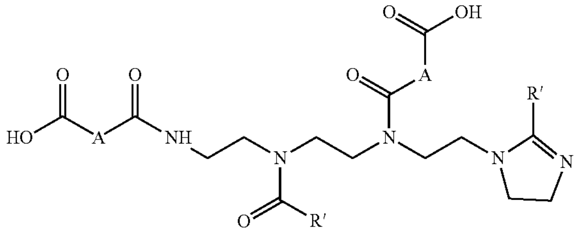

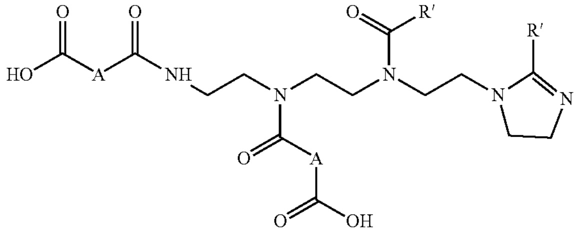

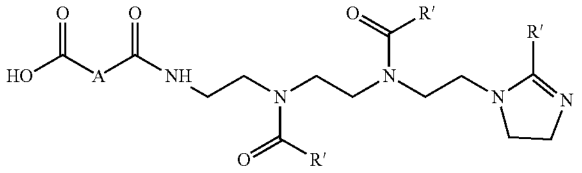

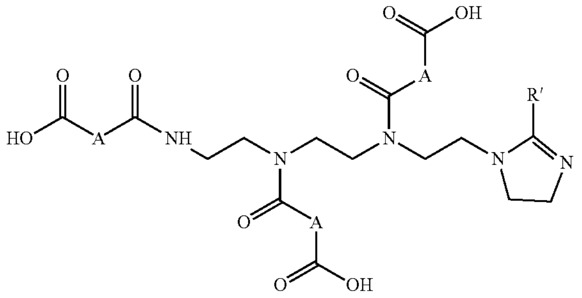

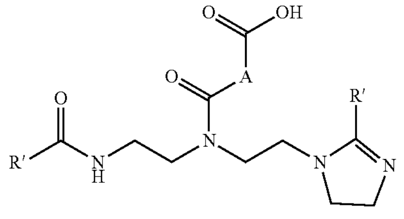

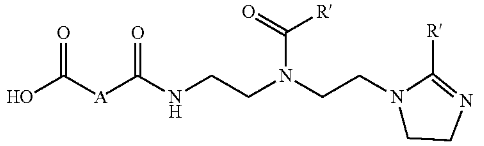

-continued

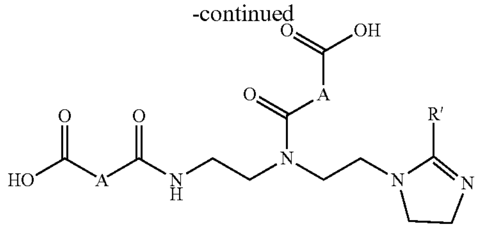

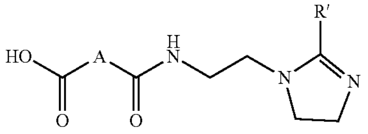

Compositions produced according to the methods herein may have a viscosity lower than some commercial wetting agents. For example, the compositions of the present disclosure may be pourable and have a viscosity of about 50 cP to about 250 cP at ambient temperature (about 60° F. to about 75° F.), or about 50 cP to about 100 cP, or about 50 cP to about 150 cP, or about 50 cP to about 200 cP, or about 100 cP to about 250 cP, or about 100 cP to about 200 cP, or about 100 cP to about 150 cP, or about 150 cP to about 250 cP, or about 150 cP to about 200 cP, or about 200 cP to about 250 cP.

The compositions of the present disclosure may have a specific gravity similar to some commercial wetting agents. For example, the compositions may have a specific gravity at ambient temperature of about 0.85 to about 0.95, or about 0.85 to about 0.9, or about 0.9 to about 0.95.

In any embodiment, the compositions described herein may be used as a component (e.g., a wetting agent) within an oil-based drilling fluid, such as an invert emulsion drilling fluid. Non-limiting examples of such drilling fluids may comprise a base fluid, wherein the base fluid is an invert emulsion comprising an oil and water, and a wetting agent comprising a composition defined above. The drilling fluids may optionally comprise one or more further additives, as described subsequently.

The drilling fluids of the present disclosure may be used in various drilling operations. Such methods may comprise operating a drill in a wellbore in the presence of a drilling fluid of the present disclosure. To drill a subterranean well, a drill string, including a drill bit and drill collars to weight the drill bit, may be inserted into a predrilled hole and rotated to cause the drill bit to cut into the rock at the bottom of the hole. The drilling operation produces rock fragments, which may be referred to as cuttings. To remove the rock fragments from the bottom of the wellbore, a drilling fluid of the present disclosure may be pumped down through the drill string to the drill bit. The drilling fluid cools the drill bit and lifts the rock fragments away from the drill bit. Eventually, the drilling fluid carries the rock fragments to the surface. At the surface, the cuttings may be removed from the drilling fluid through a secondary operation, and the drilling fluid may be recirculated back through the drill string to perform further cooling and removal of rock fragments. Additionally, the drilling fluid may absorb gases in the borehole, such as carbon dioxide, hydrogen sulfide, and methane, and transport the gases to the borehole surface for release, sequestration, or burn-off.

Drilling fluids include drilling muds, packer fluids, and completion fluids. As used herein, "drilling fluid" means any fluid used to aid the drilling of boreholes into a subterranean formation. As used herein, "completion fluids" are solids-free fluids used to "complete" an oil or gas well. Specifically, such fluids are placed in a well to facilitate final operations prior to initiation of production, such as setting screens, production liners, downhole valves, or shooting perforations into the producing zone. The fluid is meant to control a well should downhole hardware fail, without damaging the producing formation or completion components. As used herein, a "packer fluid" is a fluid that is left in the annular region of a well between tubing and outer casing above a packer. The main functions of a packer fluid are: (1) to provide hydrostatic pressure in order to lower differential pressure across the scaling element, (2) to lower differential pressure on the wellbore and casing to prevent collapse, and (3) to protect metals and elastomers from corrosion.

In addition to the foregoing, the drilling fluid also may provide cooling and lubrication of the bit and drill string utilized in boring operations. The drilling fluid additionally provides buoyancy to the drill string, relieving the tension on the drill string as the length of the borehole increases. The drilling fluid may provide hydrostatic pressure in the borehole to provide support to the sidewalls of the borehole and prevent the sidewalls from collapsing and caving in on the drill string. Additionally, the drilling fluid may provide hydrostatic pressure in the bore to prevent fluids in the downhole formations from flowing into the borehole during drilling operations.

The base fluid of the drilling fluids of the present disclosure may be a water-in-oil emulsion known as an invert emulsion. In water-in-oil emulsions or invert emulsions, oil is a continuous phase and water is dispersed in the continuous oil phase by emulsification so that the drilling fluid does not have a distinct water layer. The oil may be a natural or synthetic oil. For example, the oil may comprise diesel, kerosene, fuel oil, crude oil, mineral oil, or any combination thereof. The water in the base fluid may include one or more of deionized, tap, distilled, or fresh waters; natural, brackish, and saturated salt waters; natural, salt dome, hydrocarbon formation, produced, or synthetic brines; filtered or untreated seawaters; mineral waters; and other potable and non-potable waters containing one or more dissolved salts, minerals, or organic materials. A brine may be chosen as a preferred internal phase, such as to maintain the osmotic balance between the fluid and the formation. For example, the brine may comprise a salt (e.g., calcium chloride) at a concentration between about 10 wt % and about 45 wt % (or about 20 wt % to about 45 wt %, or about 30 wt % to about 45 wt %, or about 40 wt % to about 45 wt %) based on the total weight of the brine as the internal phase.

In one or more embodiments, the base fluid may comprise an oil-to-water ratio by volume of about 50:50 to about 95:5. For example, the oil-to-water ratio by volume of the base fluid may be about 50:50 to about 80:20, or about 50:50 to about 75:25, or about 55:45 to about 85:15, or about 60:40 to about 85:15, or about 70:30 to about 85:15, or about 60:40 to about 80:20, or about 65:35 to about 75:25.

The drilling fluid may, for example, have a weight percent of base fluid of about 1 wt % to about 99 wt %, or about 20 wt % to about 80 wt %, or about 30 wt % to about 70 wt %, or about 40 wt % to about 60 wt %, or about 45 wt % to about 55 wt % based on the total weight of the drilling fluid. In one or more embodiments, the drilling fluid comprises an amount of base fluid which is dependent upon application. For example, the amount of oil or the oil-to-water ratio may be chosen to provide a specified mud weight.

The drilling fluid may comprise one or more additives to enhance at least one characteristic of the drilling fluid. Examples of suitable additives include, but are not limited to, a primary emulsifier, a viscosifier, a weighting material, an emulsifier, a fluid-loss control additive, an alkaline compound, the like, or any combination thereof.

In any embodiment, additives in the drilling fluid may include a primary emulsifier. For example, the drilling fluid may comprise about 7 $lb_m$/bbl to about 25 $lb_m$/bbl of emulsifier, or about 8 $lb_m$/bbl to about 20 $lb_m$/bbl of emulsifier, or about 9 $lb_m$/bbl to about 15 $lb_m$/bbl of emulsifier. Examples of commercially available emulsifiers include VERSAMUL™ from MI SWACO and LE SUPERMUL™ from Halliburton Energy Services, Inc.

A viscosifier may be present in the drilling fluids to impart non-Newtonian fluid rheology to facilitate lifting of rock cuttings to the surface of the wellbore. Examples of viscosifiers may include, but are not limited to, organophilic clay, xanthan gum, polyacrylamide, the like, and any combination thereof.

In any embodiment, additives in the drilling fluid may include a weighting material. The weighting material may have a specific gravity suited for raising the density of the drilling fluid. In one or more embodiments, the weighting material may be a particulate solid having a specific gravity sufficient to increase the density of the drilling fluid by a specified amount without introducing excessive weighting material to compromise circulation of the drilling fluid through the wellbore. The weighting material may, for example, have a specific gravity of about 2 g/$cm^3$ to about 6 g/$cm^3$, or about 2 g/$cm^3$ to about 4 g/$cm^3$, or about 4 g/$cm^3$ to about 6 g/$cm^3$. Examples of weighting materials include, but are not limited to, barite, calcium carbonate, siderite, ilmenite, the like, or any combination thereof. Some example drilling fluids may include barite as the weighting material.

In non-limiting examples, the drilling fluid may, for example, have a density of about 5 $lb_m$/gal to about 15 $lb_m$/gal, or about 5 $lb_m$/gal to about 12.5 $lb_m$/gal, or about 5 $lb_m$/gal to about 10 $lb_m$/gal, or about 5 $lb_m$/gal to about 7.5 $lb_m$/gal, or about 7.5 $lb_m$/gal to about 15 $lb_m$/gal, or about 7.5 $lb_m$/gal to about 12.5 $lb_m$/gal, or about 7.5 $lb_m$/gal to about 10 $lb_m$/gal, or about 10 $lb_m$/gal to about 15 $lb_m$/gal, or about 10 $lb_m$/gal to about 12.5 $lb_m$/gal, or about 12.5 $lb_m$/gal to about 15 $lb_m$/gal.

In any embodiment, additives in the drilling fluid may include a fluid-loss control additive. The fluid-loss control additive may be added to the drilling fluid to reduce the amount of filtrate lost from the drilling fluid into a subterranean formation. Examples of fluid-loss control additives include lignite, bentonite, manufactured polymers, thinners, deflocculants, or any combination thereof. The drilling fluid may, for example, comprise about 1 $lb_m$/bbl to about 10 $lb_m$/bbl of fluid-loss control additive, or about 1 $lb_m$/bbl to about 6 $lb_m$/bbl of fluid-loss control additive, or about 1.5 $lb_m$/bbl to about 8 $lb_m$/bbl of fluid-loss control additive, or about 1.5 $lb_m$/bbl to about 2.5 $lb_m$/bbl of fluid-loss control additive. Commercially available example fluid-loss control additives include VERSACOAT™, VERSATROL™, VERSALIG™, ECOTROL™ RD, ONETROL™ HT, EMI 789, and NOVATECH™ F, all from MI SWACO, and DURATONE® HT which is from Halliburton Energy Services, Inc. In one or more embodiments, the fluid-loss control additive may be a methylstyrene/acrylate copolymer filter control agent such as ADAPTA®, which is commercially available from Halliburton Energy Services, Inc.

In any embodiment, additives in the drilling fluid may include one or more alkaline compounds for pH adjustment, which may include lime (calcium hydroxide or calcium oxide), soda ash (sodium carbonate), sodium hydroxide, potassium hydroxide, other strong bases, or any combination thereof. Conjugate bases to acids with a $pK_a$ of more than about 13 are considered strong bases. The pH may be maintained within a range suitable to minimize corrosion caused by the drilling fluid on steel tubulars, tanks, pumps, and other equipment contacting the drilling fluid. Additionally, the alkaline compounds may react with gases, such as carbon dioxide or hydrogen sulfide, for example, which may be encountered by the drilling fluid during drilling operations to prevent the gases from hydrolyzing one or more components of the drilling fluid. Some example drilling fluids may include about 0.1 $lb_m$/bbl to about 10 $lb_m$/bbl of alkaline compound, or about 0.5 $lb_m$/bbl to about 5 $lb_m$/bbl of alkaline compound, or about 1 $lb_m$/bbl to about 2 $lb_m$/bbl of alkaline compound.

One skilled in the art can appreciate that the drilling fluid may include one or more further additives to alter a characteristic of the drilling fluid. Examples of further additives may include, but are not limited to, pH adjusters, electrolytes, glycols, glycerol, dispersion aids, corrosion inhibitors, defoamers, the like, and any combination thereof.

During circulation of the drilling fluid through the wellbore, the drilling fluid may accumulate cuttings and other solids. Additionally, the drilling fluid itself may have solids dispersed throughout, such as weighting material. During circulation of the drilling fluid, the solids are continuously mixed and suspended within the drilling fluid. However, when circulation of the drilling fluid is interrupted or terminated, the solids may settle or separate from the bulk of the drilling fluid based on the rheology of the drilling fluid. Settling of the cuttings and other solids is undesirable because they would accumulate at the bottom of the wellbore and potentially prevent the drill from rotating or completely block the flow path of the drilling fluid upon resumption of drilling activities.

The viscosifier may also adjust the rheology and viscosity of the drilling fluid when combined with the base fluid and one or more additives. The addition of the viscosifier may result in an increased yield point and gel strength. Increased viscosity, yield point, and gel strength may assist in maintaining suspension of solids and cuttings within the drilling fluid composition both during circulation and when circulation is interrupted.

The viscosity of the drilling fluid may be measured using a standard oilfield viscometer according to test methods provided in the American Petroleum Institute (API) Recommended Practice for Field Testing Oil-Based Drilling Fluids (RP 13B-2/ISO 10414-1:2002) published August 2014 and incorporated by reference into this disclosure in its entirety. Drilling fluid is placed in an annular space between two concentric cylinders. The outer cylinder is rotated at a constant rotational velocity which produces a torque on the inner cylinder (or spindle) which is measured. The viscosity is reported as shear stress in units of pounds of force per 100 square feet ($lb_f$/100 $ft^2$). The viscometer, which may be a Fann 35 from Fann Instruments, may be used to measure the shear rate of the drilling fluid compositions.

The gel strength refers to the shear stress of the drilling fluid measured at a low shear rate following a defined period of time during which the drilling fluid is maintained in a static state. The shear stress at low shear rate may be measured using a standard oilfield viscometer operated at low rpms, such as about 3 rpm, according to the test methods described in API RP 13B-2. To measure the gel strength, the drilling fluid is first stirred by contacting the drilling fluid with the spindle of the viscometer and operating the viscometer at 600 rotations per minute (rpm) for 10 seconds. The viscometer is then turned off for a period of time (time period). For a 10 second gel strength, the time period is 10 seconds, and for a 10 minute gel strength, the time period is 10 minutes. Other time periods for measuring gel strength are contemplated. During the time period, the drilling fluid comes to rest in a static state. Upon expiration of the time period, the viscometer is turned back on at a low speed, such as 3 rpm, to generate a low shear rate. The viscometer reading is then taken. The gel strength is reported in units of pounds of force per 100 square feet ($lb_f$/100 $ft^2$).

The 10 second gel strength provides an indication of the ability of the drilling fluid to gel immediately upon termination of drill rotation and circulation of the drilling fluid composition. Quick or near instantaneous gelling of the drilling fluid composition upon termination of circulation helps ensure solids do not settle before gelling. A sufficiently high 10 second gel strength indicates the drilling fluid composition formed a robust gel quickly after removal of agitation. The drilling fluid may, for example, have a 10 second gel strength at ambient temperature of about 15 $lb_f$/100 $ft^2$ to about 30 $lb_f$/100 $ft^2$, or about 15 $lb_f$/100 $ft^2$ to about 25 $lb_f$/100 $ft^2$, or about 15 $lb_f$/100 $ft^2$ to about 20 $lb_f$/100 $ft^2$, or about 20 $lb_f$/100 $ft^2$ to about 30 $lb_f$/100 $ft^2$, or about 20 $lb_f$/100 $ft^2$ to about 25 $lb_f$/100 $ft^2$, or about 25 $lb_f$/100 $ft^2$ to about 30 $lb_f$/100 $ft^2$.

Similarly, the 10 minute gel strength provides an indication of the ability of the drilling fluid to sustain a gelled configuration for a sustained period after termination of drill rotation and circulation of the drilling fluid. A sufficiently high 10 minute gel strength indicates the drilling fluid formed a robust gel which was maintained during periods without agitation. The drilling fluid may, for example, have a 10 minute gel strength at ambient temperature of about 15 $lb_f$/100 $ft^2$ to about 30 $lb_f$/100 $ft^2$, or about 15 $lb_f$/100 $ft^2$ to about 25 $lb_f$/100 $ft^2$, or about 15 $lb_f$/100 $ft^2$ to about 20 $lb_f$/100 $ft^2$, or about 20 $lb_f$/100 $ft^2$ to about 30 $lb_f$/100 $ft^2$, or about 20 $lb_f$/100 $ft^2$ to about 25 $lb_f$/100 $ft^2$, or about 25 $lb_f$/100 $ft^2$ to about 30 $lb_f$/100 $ft^2$.

The drilling fluid behaves as a rigid body at low stress, but flows as a viscous fluid at a higher shear stress. The rheology of the drilling fluid may be modeled based on Bingham plastic flow behavior. Additionally, the rheological behavior of the drilling fluid may be determined by measuring the shear stress on the drilling fluid at different shear rates, which may be accomplished by measuring the shear stress, the shear rate, or both on the drilling fluid using a viscometer (Fann 35 rheometer) at 3 rpm, 6 rpm, 300 rpm, and 600 rpm.

The rheology of the drilling fluid may be evaluated from the plastic viscosity (PV) and yield point (YP), which are parameters from the Bingham plastic rheology model.

The PV is related to the resistance of the drilling fluid to flow due to mechanical interaction between the solids of the drilling fluid and represents the viscosity of the drilling fluid extrapolated to infinite shear rate. The PV reflects the type and concentration of the solids in the drilling fluid, and a lesser PV is preferred. The PV of the drilling fluid may be estimated by measuring the shear rate of the drilling fluid using the viscometer at spindle speeds of 300 rpm and 600 rpm and subtracting the 300 rpm measurement from the 600 rpm measurement according to Equation 1. The PV is provided in this disclosure in units of centipoise (cP).

$$PV=(600\ rpm\ \text{reading})-(300\ rpm\ \text{reading}) \qquad \text{Equation 1}$$

The drilling fluid may, for example, have a PV at ambient temperature of about 50 cP to about 75 cP, or about 50 cP to about 65 cP, or about 50 cP to about 60 cP, or about 60 cP to about 75 cP, or about 60 cP to about 65 cP, or about 65 cP to about 75 cP.

The YP represents the shear stress below which the drilling fluid behaves as a rigid body and above which the drilling fluid flows as a viscous fluid. Specifically, the YP represents the amount of stress required to move the drilling fluid from a static condition. The YP is expressed as a force per area, such as pounds of force per one hundred square feet ($lb_f/100\ ft^2$). YP provides an indication of the carrying capacity of the drilling fluid for rock cuttings through the annulus, which provides an indication of the hole-cleaning ability of the drilling fluid. Additionally, frictional pressure loss is directly related to the YP. For higher YPs, there will be higher pressure loss while the drilling fluid is being circulated. A drilling fluid having a YP of equal to or greater than 15 $lb_f/100\ ft^2$ is considered acceptable for drilling and a YP of equal to or greater than 30 $lb_f/100\ ft^2$ is considered acceptable for utilization as a packer fluid. The YP is determined by extrapolating the Bingham plastic rheology model to a shear rate of zero. The YP may be estimated from the PV from Equation 1 by subtracting the PV obtained from Equation 1 from the shear rate of the drilling fluid measured at 300 rpm according to Equation 2.

$$YP = (300\ rpm\ \text{reading}) - PV \qquad \text{Equation 2}$$

The drilling fluid may, for example, have a YP at ambient temperature of about 40 $lb_f/100\ ft^2$ to about 60 $lb_f/100\ ft^2$, or about 40 $lb_f/100\ ft^2$ to about 50 $lb_f/100\ ft^2$, or about 50 $lb_f/100\ ft^2$ to about 60 $lb_f/100\ ft^2$.

Embodiments disclosed herein include:

A. Pourable wetting agent compositions, the compositions including a first condensation reaction product having a structure represented by

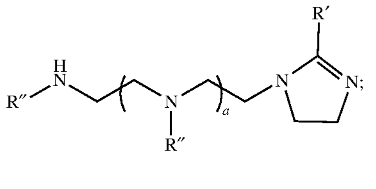

wherein: a is 0 or a positive integer; R' is a $C_6$-$C_{30}$ hydrocarbyl group; and R" is —CO—R' or —CO-A-COOH, provided that at least one occurrence of R" is —CO-A-COOH; wherein A is a divalent hydrocarbyl group.

B. Methods associated with pourable wetting agents, the methods including providing a composition comprising a first amidated imidazoline having a structure represented by

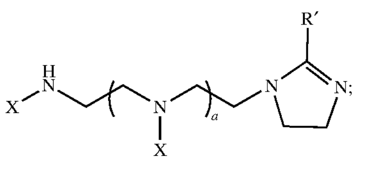

wherein a is 0 or a positive integer; R' is a $C_6$-$C_{30}$ hydrocarbyl group; and X is H or —CO—R', provided that at least one occurrence of X is H; combining the composition with a dicarboxylic acid having a formula of HOOC-A-COOH to form a reaction mixture; wherein A is a divalent hydrocarbyl group; and heating the reaction mixture at a first reaction temperature for a first time period to form a second amidated imidazoline having a structure represented by

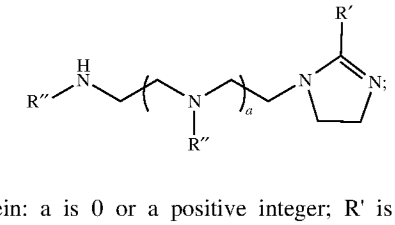

wherein: a is 0 or a positive integer; R' is a $C_6$-$C_{30}$ hydrocarbyl group; and R" is —CO—R' or —CO-A-COOH, provided that at least one occurrence of R" is —CO-A-COOH.

C. Drilling Fluids. The drilling fluids comprise an invert emulsion comprising an oil and water; and the composition of A, optionally wherein the drilling fluids further comprise an additive comprising at least one material selected from the group consisting of a primary emulsifier, a viscosifier, a weighting material, a fluid-loss control additive, an alkaline compound, and any combination thereof.

D. Drilling methods. The methods comprise operating a drill in a wellbore in the presence of the drilling fluid of C.

Each of embodiments A-D may have one or more of the following additional elements in any combination:

Element 1: wherein the composition further comprises a second condensation reaction product having a structure represented by

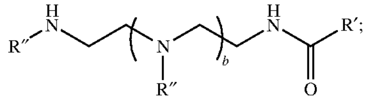

wherein: b is a positive integer; R' is a $C_6$-$C_{30}$ hydrocarbyl group; and R" is —CO—R' or —CO-A-COOH, provided that at least one occurrence of R" is —CO-A-COOH.

Element 2: wherein b is 1, 2, or 3.

Element 3: wherein A is a $C_1$-$C_3$ alkyl group, a $C_2$-$C_3$ alkenyl group, or a $C_2$-$C_3$ alkynyl group.

Element 4: wherein R' is a $C_6$-$C_{30}$ alkyl group.

Element 5: wherein a is 0, 1, or 2.

Element 6: wherein each R' is the same.

Element 7: wherein R' comprises an unsaturated hydrocarbyl group.

Element 8: wherein a is 1 or 2.

Element 9: wherein the dicarboxylic acid comprises maleic acid, fumaric acid, succinic acid, malonic acid, glutaric acid, glutaconic acid, or any combination thereof.

Element 10: wherein the first reaction temperature is at least about 180° C. and the first time period is at least about 5 hours.

Element 11: wherein providing the composition comprises contacting a fatty acid having a formula of R'—COOH with a polyamine in the presence of an acid catalyst; forming a first amidated polyamine under a first set of conditions; and converting at least a portion of the first amidated polyamine to a first amidated imidazoline under a second set of conditions.

Element 12: wherein the polyamine comprises diethylenetriamine, triethylenetetramine, tetraethylenepentamine, or any combination thereof.

Element 13: wherein the first set of conditions comprises a second reaction temperature of at least about 160° C. and a second time period of at least about 4 hours.

Element 14: wherein the second set of conditions comprises a third reaction temperature of at least about 180° C. and a third time period of about 2 hours to about 3 hours.

By way of non-limiting example, exemplary combinations applicable to A-D include, but are not limited to: 1 with 2; 1 with 3; 1 with 4; 1 with 5; 2 with 3; 2 with 4; 2 with 5; 3 with 4; 3 with 5; 4 with 5; 9 with 10; 9 with 11; 10 with 11; 11 with 12; 11 with 13; 11 with 14; 12 with 13; 12 with 14; 13 with 14; 1 with 2 and 3; 1 with 3 and 4; and 1 with 4 and 5.

The present disclosure is further directed to the following non-limiting causes:

Clause 1. A composition comprising:

a first condensation reaction product having a structure represented by

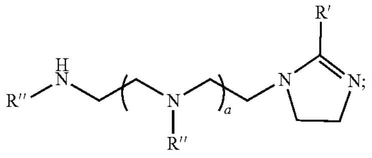

wherein: a is 0 or a positive integer;

R' is a $C_6$-$C_{30}$ hydrocarbyl group; and

R" is —CO—R' or —CO-A-COOH, provided that at least one occurrence of R" is CO-A-COOH; wherein A is a divalent hydrocarbyl group.

Clause 2. The composition of clause 1, further comprising: a second condensation reaction product having a structure represented by

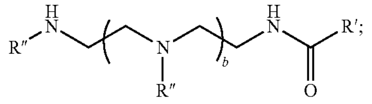

wherein:

b is a positive integer;

R' is a $C_6$-$C_{30}$ hydrocarbyl group; and

R" is —CO—R' or —CO-A-COOH, provided that at least one occurrence of R" is —CO-A-COOH.

Clause 3. The composition of clause 2, wherein b is 1, 2, or 3.

Clause 4. The composition of any one of clauses 1-3, wherein A is a $C_1$-$C_3$ alkyl group, a $C_2$-$C_3$ alkenyl group, or a $C_2$-$C_3$ alkynyl group.

Clause 5. The composition of any one of clauses 1-4, wherein R' is a $C_6$-$C_{30}$ alkyl group.

Clause 6. The composition of any one of clauses 1-5, wherein a is 0, 1, or 2.

Clause 7. A drilling fluid comprising:

an invert emulsion comprising an oil and water; and the composition of any one of clauses 1-6.

Clause 8. The drilling fluid of clause 7, further comprising:

an additive comprising at least one material selected from the group consisting of a primary emulsifier, a viscosifier, a weighting material, a fluid-loss control additive, an alkaline compound, and any combination thereof.

Clause 9. A drilling method comprising:

operating a drill in a wellbore in the presence of the drilling fluid of clause 7 or clause 8.

Clause 10. A method comprising:

providing a composition comprising a first amidated imidazoline having a structure represented by

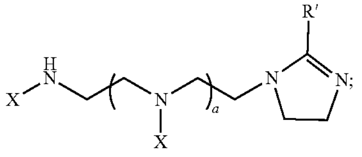

wherein:

a is O or a positive integer;

R' is a $C_6$-$C_{30}$ hydrocarbyl group; and

X is H or —CO—R', provided that at least one occurrence of X is H;

combining the composition with a dicarboxylic acid having a formula of HOOC-A-COOH to form a reaction mixture;

wherein A is a divalent hydrocarbyl group; and heating the reaction mixture at a first reaction temperature for a first time period to form a second amidated imidazoline having a structure represented by

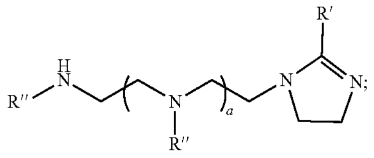

wherein:

a is O or a positive integer;

R' is a $C_6$-$C_{30}$ hydrocarbyl group; and

R" is —CO—R' or —CO-A-COOH, provided that at least one occurrence of R" is —CO-A-COOH.

Clause 11. The method of clause 10, wherein the composition further comprises a first amidated polyamine having a structure represented by

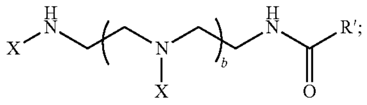

wherein:

b is a positive integer;

R' is a $C_6$-$C_{30}$ hydrocarbyl group; and

X is H or —CO—R', provided that at least one occurrence of X is H; and wherein a second amidated polyamine having a structure represented by

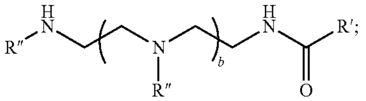

forms during the first time period;

wherein:

b is a positive integer;

R' is a $C_6$-$C_{30}$ hydrocarbyl group; and

R" is —CO—R' or —CO-A-COOH, provided that at least one occurrence of R" is —CO-A-COOH.

Clause 12. The method of clause 11, wherein b is 1, 2, or 3.

Clause 13. The method of any one of clauses 10-12, wherein the dicarboxylic acid comprises maleic acid, fumaric acid, succinic acid, malonic acid, glutaric acid, glutaconic acid, or any combination thereof.

Clause 14. The method of any one of clauses 10-13, wherein R' is a $C_6$-$C_{30}$ alkyl group.

Clause 15. The method of any one of clauses 10-14, wherein a is 0, 1, or 2.

Clause 16. The method of any one of clauses 10-15, wherein the first reaction temperature is at least about 180° C. and the first time period is at least about 5 hours.

Clause 17. The method of any one of clauses 10-16, wherein providing the composition comprises:

contacting a fatty acid having a formula of R'—COOH with a polyamine in the presence of an acid catalyst;

forming a first amidated polyamine under a first set of conditions; and converting at least a portion of the first amidated polyamine to a first amidated imidazoline under a second set of conditions.

Clause 18. The method of clause 17, wherein the polyamine comprises diethylenetriamine, triethylenetetramine, tetraethylenepentamine, or any combination thereof.

Clause 19. The method of clause 17 or clause 18, wherein the first set of conditions comprises a second reaction temperature of at least about 160° C. and a second time period of at least about 4 hours.

Clause 20. The method of any one of clauses 17-19, wherein the second set of conditions comprises a third reaction temperature of at least about 180° C. and a third time period of about 2 hours to about 3 hours.

EXAMPLES

Experimental Wetting Agent. A mixture of $C_{12}$-$C_{14}$ fatty acids (48.84 g) was preheated to 85° C. The fatty acids were then added to a reactor at 100° C. under a nitrogen blanket with the agitator engaged. The reflux condenser of the reactor was left open to allow removal of water formed during the reaction. The reactor was then charged with 0.06 g of p-toluenesulfonic acid (PTSA) and the temperature was raised to 130° C. Triethylenetetramine was added to the reactor slowly, and the temperature was raised to 160° C. for 4 hours. When water evolution had stopped, the reactor temperature was further raised to 180° C. for about 2 hours to promote imidazoline formation. A sample of the imidazoline was removed for further analysis. A slight excess of maleic acid was then added to the reactor and reacted with the imidazoline for about 5.5 hours at 180° C. to produce an amidated imidazoline as an experimental wetting agent.

Figure 1B:
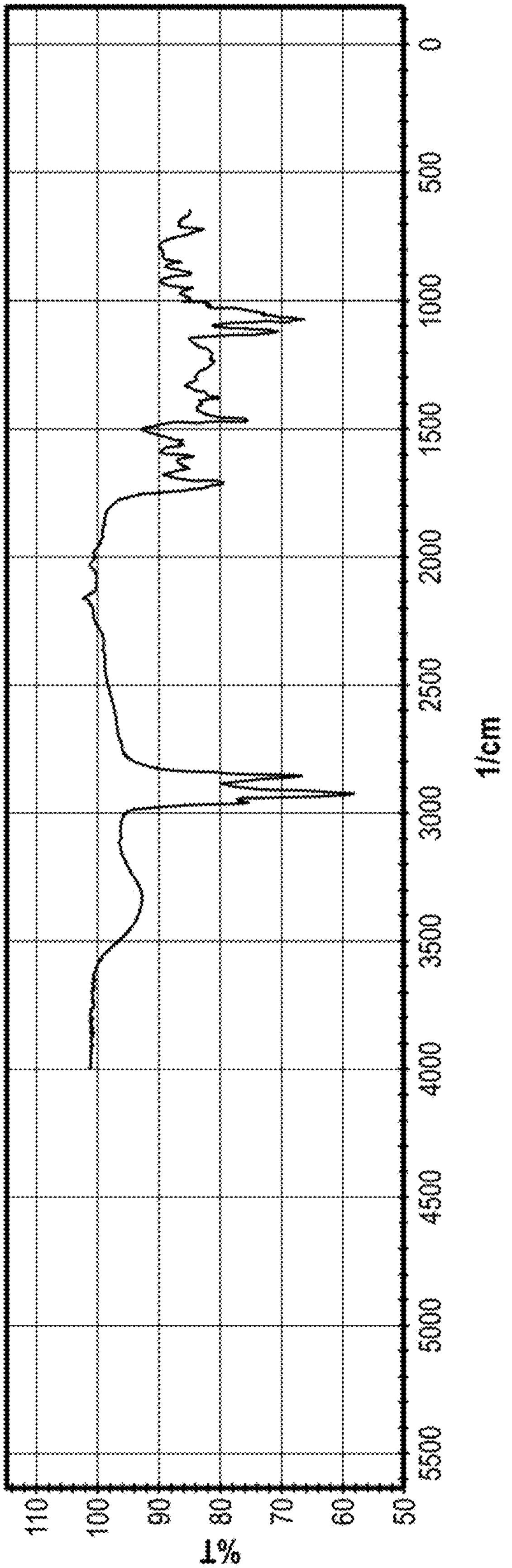
FIG. 1B is an illustrative FTIR spectrum of an experimental wetting agent produced from an amidated imidazoline.

FIG. 1A is an illustrative FTIR spectrum of the imidazoline before reaction with the maleic acid. FIG. 1B is an illustrative FTIR spectrum of the experimental wetting agent. The FTIR spectra, specifically the C═O stretching at 1640 $cm^{-1}$, demonstrate that the imidazoline was further converted into the example wetting agent, specifically a condensation reaction product of maleic acid with residual amines in the imidazoline.

Table 1 shows selected chemical and physical properties of the experimental wetting agent versus a comparative wetting agent lacking maleic acid modification but otherwise similar to the experimental wetting agent. The values in Table 1 are reported at 60° F.

TABLE 1

| | Comparative Wetting Agent | Experimental Wetting Agent |
|---|---|---|
| Acid number | 12.98 | 82.59 |
| Base number | 38.38 | 10.84 |
| Specific gravity | 0.911 | 0.915 |
| Viscosity (cP) | Unpourable | 110 |

The experimental wetting agent showed reduced viscosity relative to the comparative wetting agent while maintaining a similar density.

The comparative and experimental wetting agents were used to prepare comparative and experimental oil-based drilling fluids, respectively. Other than the wetting agent, the oil-based drilling fluids were formulated identically. Table 2 shows the composition of the drilling fluids. The density of both drilling fluids was 12 lb/gal.

TABLE 2

| Component | Concentration (wt %) |
|---|---|
| Diesel | 36.59 |
| CLAYTONE ® HT | 0.99 |
| ENDURAMOD ® | 0.60 |
| Lime | 0.60 |
| PINEMUL 210 ® | 1.59 |
| Deionized water | 11.40 |
| Anhydrous calcium chloride | 3.80 |
| Barite | 43.65 |
| Wetting agent | 0.79 |

Table 3 shows the rheological characteristics of the comparative and experimental drilling fluids obtained using a Fann® 35 Dial Reading (DR) at 60° F. and 150° F. after aging the drilling fluids for 16 hours.

TABLE 3

| | Comparative Drilling Fluid | | Experimental Drilling Fluid | |
|---|---|---|---|---|
| | 60° F. | 150° F. | 60° F. | 150° F. |
| Shear rate, 600 rpm ($s^{-1}$) | 172 | 85 | 174 | 80 |
| Shear rate, 300 rpm ($s^{-1}$) | 107 | 61 | 114 | 52 |
| Shear rate, 200 rpm ($s^{-1}$) | 84 | 49 | 97 | 43 |
| Shear rate, 100 rpm ($s^{-1}$) | 58 | 36 | 69 | 32 |
| Shear rate, 6 rpm ($s^{-1}$) | 24 | 16 | 32 | 16 |
| Shear rate, 3 rpm ($s^{-1}$) | 23 | 14 | 30 | 14 |
| 10 s gel strength (lb/100 $ft^2$) | 23 | 13 | 26 | 13 |
| 10 min gel strength (lb/100 $ft^2$) | 25 | 14 | 29 | 15 |
| 30 min gel strength (lb/100 $ft^2$) | 27 | 15 | 31 | 15 |
| Plastic Viscosity (cP) | 65 | 24 | 60 | 28 |
| Yield Point (1b/100 $ft^2$) | 42 | 37 | 54 | 24 |

As shown in Table 3, no significant rheological changes were observed between the comparative and experimental oil-based drilling fluids. Excellent rheological properties and similar gel strengths were exhibited by both oil-based drilling fluids, with low rotation per minute (RPM; proportional to shear rate) readings and yield points (YPs) greater than 8 lb/100 $ft^2$, indicating effective suspension capabilities for heavy additives such as barite, calcium carbonate, manganese oxide, and drill cuttings.

The terminology used herein is for the purpose of describing particular embodiments only and is not intended to be limiting of the invention. As used herein, for example, the singular forms "a," "an," and "the" are intended to include the plural forms as well, unless the context clearly indicates otherwise. It will be further understood that the terms "contains," "containing," "includes," "including," "comprises," and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation used herein are merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third, etc.) is for distinction and not counting. For example, the use of "third" does not imply there must be a corresponding "first" or "second." Also, if used herein, the terms "coupled" or "coupled to" or "connected" or "connected to" or "attached" or "attached to" may indicate establishing either a direct or indirect connection, and are not limited to either unless expressly referenced as such.

While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by one or more embodiments described herein. At the very least, and not as an attempt to limit the application of the doctrine of equivalents to the scope of the claim, each numerical parameter should at least be construed in light of the number of reported significant digits and by applying ordinary rounding techniques.

The invention claimed is:

1. A composition comprising:

a first condensation reaction product having a structure represented by

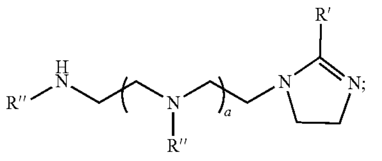

wherein:

a is 0 or a positive integer;

R' is a $C_6$-$C_{30}$ hydrocarbyl group; and

R" is-CO—R' or —CO-A-COOH, provided that at least one occurrence of R" is —CO-A-COOH;

wherein A is a divalent hydrocarbyl group;

a second condensation reaction product having a structure represented by

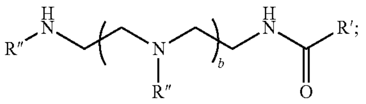

wherein:

b is a positive integer;

R' is a $C_6$-$C_{30}$ hydrocarbyl group; and

R" is-CO—R' or —CO-A-COOH, provided that at least one occurrence of R" is-CO-A-COOH; and wherein the first condensation product and the second condensation product have a ratio from about 100:0 to about 31:69.

2. The composition of claim 1, wherein b is 1, 2, or 3.

3. The composition of claim 1, wherein A is a $C_1$-$C_3$ alkyl group, a $C_2$-$C_3$ alkenyl group, or a $C_2$-$C_3$ alkynyl group.

4. The composition of claim 1, wherein R' is a $C_6$-$C_{30}$ alkyl group.

5. The composition of claim 1, wherein a is 0, 1, or 2.

6. A drilling fluid comprising:

an invert emulsion comprising an oil and water; and the composition of claim 1.

7. The drilling fluid of claim 6, further comprising:

an additive comprising at least one material selected from the group consisting of a primary emulsifier, a viscosifier, a weighting material, a fluid-loss control additive, an alkaline compound, and any combination thereof.

8. A drilling method comprising:

operating a drill in a wellbore in the presence of the drilling fluid of claim 6.

* * * * *